United States Patent [19]

Adam et al.

[11] Patent Number: 4,845,503

[45] Date of Patent: Jul. 4, 1989

[54] ELECTROMAGNETIC DIGITIZER

[75] Inventors: Hamish G. Adam, Flower Mound, Tex.; Peter J. Sharer, Loma Mar; P. Eric Peterson, San Mateo, both of Calif.

[73] Assignee: Western Atlas International, Inc., Houston, Tex.

[21] Appl. No.: 152,754

[22] Filed: Feb. 5, 1988

[51] Int. Cl.$^4$ ............................................. G01S 5/04
[52] U.S. Cl. .................................. 342/448; 342/451; 324/377
[58] Field of Search ............... 342/448, 451; 324/377, 324/201

[56] References Cited

U.S. PATENT DOCUMENTS

| | | |
|---|---|---|
| D. 288,815 | 3/1987 | Davies . |
| 3,792,243 | 2/1984 | Appel et al. . |
| 3,820,012 | 6/1974 | Molyneux .......................... 324/377 |
| 4,477,973 | 10/1984 | Davies . |
| 4,593,470 | 6/1986 | Davies . |
| 4,613,866 | 9/1986 | Blood .................................. 342/448 |

OTHER PUBLICATIONS

Core Laboratories Advertisement for Fractured Reservoir Description, 1987.
Core Laboratories Advertisement for Core Dip Log, 1987.
Aniyo et al, 1987, A Practical Method of Constructing Surfaces in Three-Dimensional Space, The Visual Computer, vol. 3, No. 1, pp. 4–12.
Levine, 1983, Application of Three-Dimensional Vision Systems to Industrial Robotic Manufacturing, Journal of Society for the Advancement of Materials and Process Engineering Quarterly, vol. 15, No. 1, Oct., pp. 1–5.
Schmitt et al, 1986, An Adaptive Subdivision Method for Surface.
Fitting For Sampled Data, Computer Graphics, vol. 20, No. 4, Aug., pp. 179–188.
Soroka et al, 1976, Generalized Cylinders from Serial Sections, IEEE Computer Society, Third International Joint Conference on Pattern Recognition, Nov. 8–11, pp. 734–735.

Primary Examiner—Theodore M. Blum
Attorney, Agent, or Firm—Barry C. Kane

[57] ABSTRACT

A method and apparatus is disclosed for accurately determining the spatial orientation of planar and linear features expressed along the exterior surface of a core sample. The core sample is positioned in a plurality of sequentially generated orthogonal electromagnetic fields. The core sample is retained by a device which allows complete rotation of the core sample about a predetermined axis while positioned in the electromagnetic fields. A stylus containing an antenna for detecting the electromagnetic fields is used to trace surficial features along the core exterior while simultaneously detecting components of the generated electromagnetic fields. The stylus provides an output to an analyzing device which calculates the coordinates of points along the core features. The coordinates are passed to a computer which has also been monitoring the rotation angle of the core. The data is stored and later used to calculate the spatial orientations of the structures with respect to a known reference on the core sample.

19 Claims, 8 Drawing Sheets

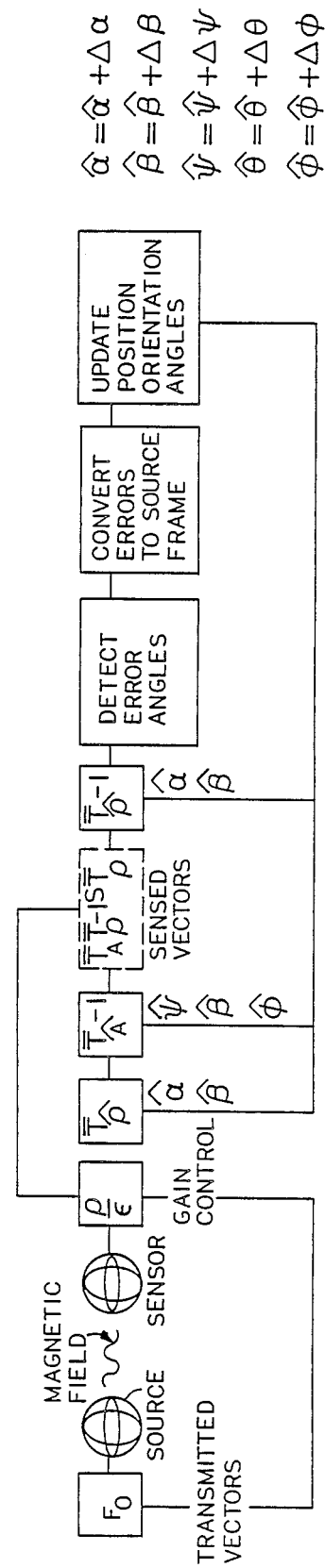
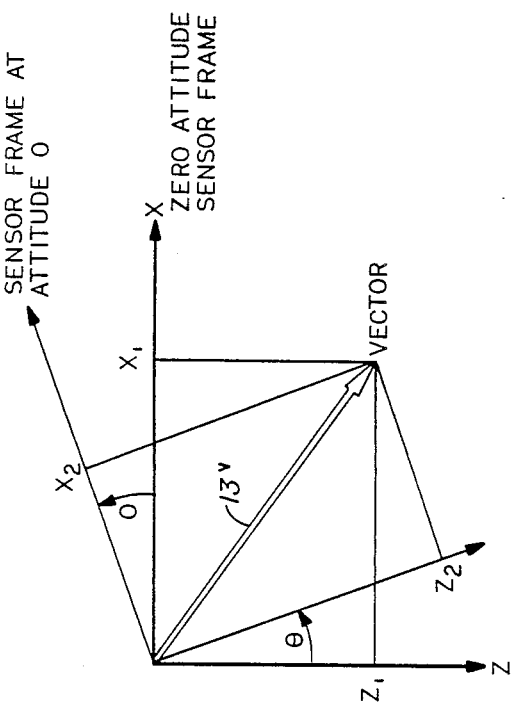
FIG. 8
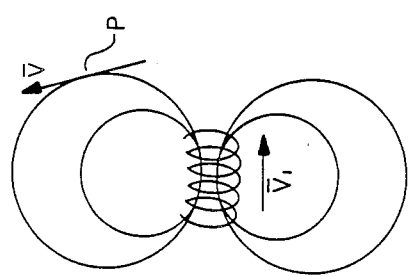
FIG. 7
FIG. 9

ELECTROMAGNETIC DIGITIZER

BACKGROUND OF THE INVENTION

This invention relates generally to devices for digitizing coordinates of a three-dimensional object, and more particularly to an apparatus for digitizing linear and planar structures exhibited in a core sample taken from the earth.

Apparatus for digitizing the coordinates of a two-dimensional figure with an electromagnetic coupling are known in the art. Such drawing and digitizing devices typically comprise a movable carriage or "mouse" which is free to move along a surface of a digitizing table. A cursor on the mouse may be placed at point on the figure to be digitized. Alternatively, the cursor may be used to trace a line on the figure for continuous digitizing. The mouse contains two electromagnetic coils which are used to produce signals indicative of the location of the mouse on the digitizing table. Such digitizing devices are only capable of determining the mouse location in two dimensions. Since the position of the cursor is restricted with respect to the digitizing table, such devices are incapable of digitizing the coordinates of a three-dimensional body.

Other devices are known for digitizing three-dimensional objects; however, these devices only employ optical couplings, acoustic couplings, manual measurements, or measurements using potentiometers and the like for determining the coordinates of the three-dimensional body.

The art of electromagnetically digitizing objects in three-dimensions has been developed by the McDonnell Douglas Corporation of St. Louis, Mo. and is disclosed in U.S. Pat. No. 4,613,866 issued Sept. 23, 1986. This device uses a hand held stylus for tracing and identifying points of interest on the surface of a stationary object. An electromagnetic source is provided immediately below a work surface upon which the object rests. A plurality of coils located within the source sequentially generate three-orthogonal electromagnetic fields, each of which are detected by similar coils located within a hand-held stylus which provides an output signal. This is output to an electronic analyzer which converts the components of the electromagnetic fields detected by the coils into a position and orientation of the stylus relative to a reference coordinate frame, thus, the coordinates of the object's surface are determined by the analyzer.

A disadvantage of this device is that the objects to be digitized must remain stationary within the electromagnetic field. Therefore, the operator must work around the object to digitize all surfaces. In the art of core analysis used in petroleum exploration, linear and planar structures of core sample have traditionally been measured manually. The information gathered from these studies were hand computed or entered into a computer for analysis. This is still very much the case today. No methods exist in core analysis for directly and quickly identifying and determining structures exhibited in core samples.

SUMMARY OF THE INVENTION

It is an object of this invention to provide a fast and efficient way to measure sedimentological and structural features of a core sample.

It is another object of this invention to provide a rapid means for analyzing and displaying data measured from a core sample.

It is yet another object of this invention to greatly enhance the accuracy and repeatability of measuring the orientation of planar and linear features in a core sample.

The inventive method and apparatus for measuring planar and linear structures exhibited along the exterior surface of a core sample comprises a means for orienting in a predetermined plane and rotating the core sample about its longitudinal axis such as a core holder having rollers. Located symmetrically adjacent the core holder is a means for inducing a plurality of orthogonal dipole magnetic fields about the core sample. The electromagnetic source consists of three ferrite core coils each oriented in plane orthogonal to the others. The coils are energized in a predetermined sequence by a cable connected transmitter located within an electronics package or analyzing unit. A stylus containing three-orthogonal ferrite-core receiving coils are located a predetermined distance from a pointer used to identify points along the core sample. The receiving coils are operably coupled by a cable to the analyzing unit and detect components of the electromagnetic fields when a switching device, such as a foot operated switch coupled to the analyzing unit, is activated. The data detected by the receiving coils is passed to the analyzer which is further passed to a computer for display. The rollers in the core holder are preferably mechanically coupled to a shaft encoder which senses the amount the core has been rotated. The output of the shaft encoder is passed to the analyzing unit to be combined with the output from the receiving coils. The three-dimensional coordinates detected by the receiving coils, combined with the data from the shaft encoder allows the operator to examine and identify features along the entire exterior surface of the core sample without removing the core from the electromagnetic fields. User friendly software driving an interconnected computer may be used to calculate core depth data as well as determine and display structure orientations and core descriptive terms. In essence, a complete core description may be compiled by collecting digital data directly from the core sample; data does not have to be collected and then manually entered into the computer.

Using the above method and apparatus, the physical determination of the orientation of the structures is greatly enhanced as far as accuracy and repeatability of the measurements. Previously, an analyst used protractors, rulers and considerable "eyeballing" to determine a features orientation. The accuracy of the previous method left much to be desired.

BRIEF DESCRIPTION OF THE DRAWINGS

A better understanding of the benefits and advantages of my invention may be obtained from the appended detailed description and drawings, wherein:

FIG. 7 illustrates a magnetic field vector $\bar{V}_2$ at a position P in a dipole magnetic field $\bar{V}_1$;

FIG. 8 illustrates the source transfer function for a sensor related through an elevational angle;

FIG. 9 is a flow diagram illustrating the computation strategy of the digitizer;

DETAILED DESCRIPTION OF THE PREFERRED EMBODIMENTS

Figure 1A:
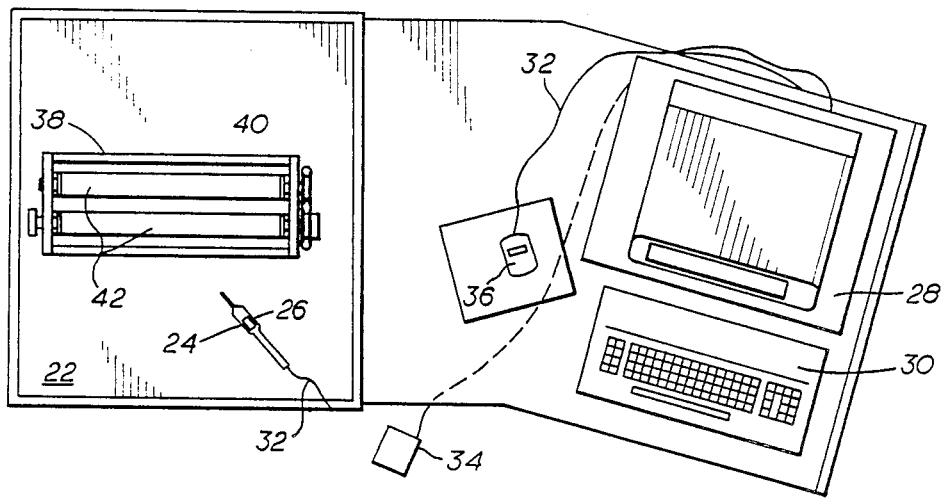
FIG. 1 is a general illustration of one embodiment of the three-dimensional digitizer.
Figure 1B:
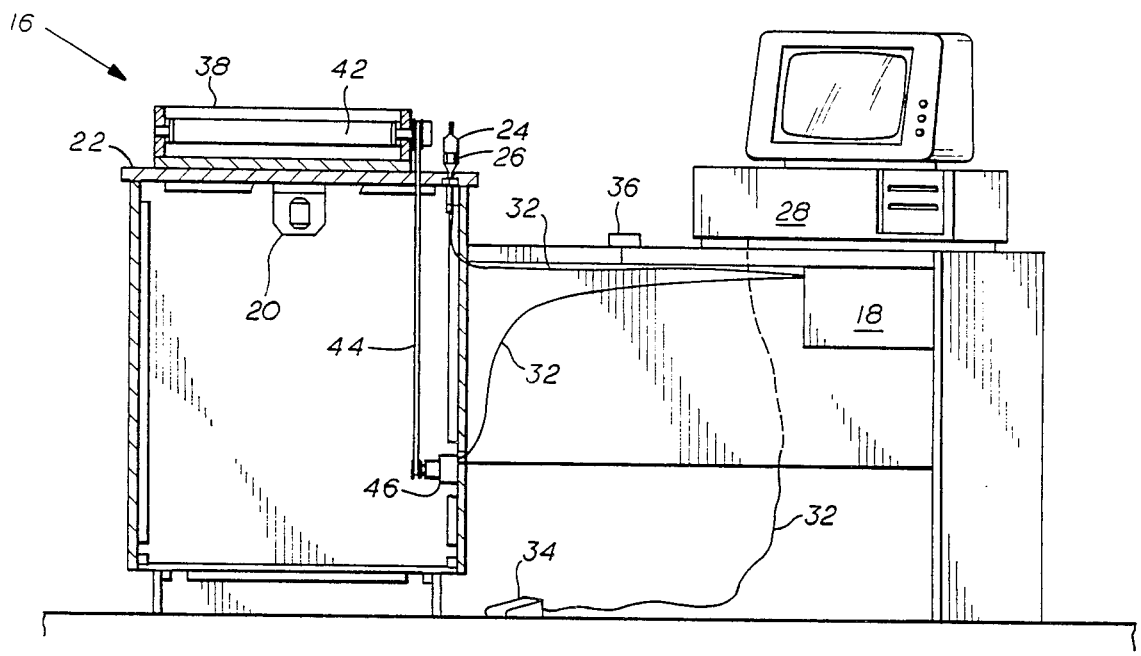

FIG. 1 is a general illustration of one embodiment of the three-dimensional digitizer 16. The digitizer 16 is basically comprised of an analyzing unit 18, a source of electromagnetic radiation 20 located just below a work surface 22, a stylus 24 containing several antenna 26, and a computer 28 having a keypad 30. The analyzing unit 18 is operably coupled to each of the above devices by way of cables 32. Accessory devices such as foot activated switch 34 and a mouse 36 may also be coupled to the analyzing unit 18 and computer 28 respectively. Located on the work surface 22 and centrally positioned above the radiation source 20 is a means 38 for rotating and retaining a length of a core sample 40, generally comprised of two parallel rollers 42. The rollers 42 are spaced sufficiently close together so as to hold a core sample of two-inch diameter or larger. This core holding device will be described in greater detail below. The rollers 42 of the core holder 38 are mechanically coupled via a belt 44 to a shaft encoder means 46 for measuring the rotation angle of the rollers 42. As shown in FIG. 1(b), the shaft encoder 46 is preferably located a predetermined distance directly below the core holder 38 in a manner such that the belt 44 is unimpeded. The shaft encoder 46 is operably coupled via a cable 32 with the computer 28.

Each of the devices interfaced with the analyzing unit 18 either receive input from, or provide output to the unit 18. The output of the analyzer unit 18 is typically transmitted to the computer 28 where a preferred user-friendly software package is used to transform digitized coordinates of structures traced along the core sample into information such as Rose diagrams, stereo plots and dip plots. This output from the computer is typically routed to a peripheral device such as a printer or plotter.

Figure 2A:
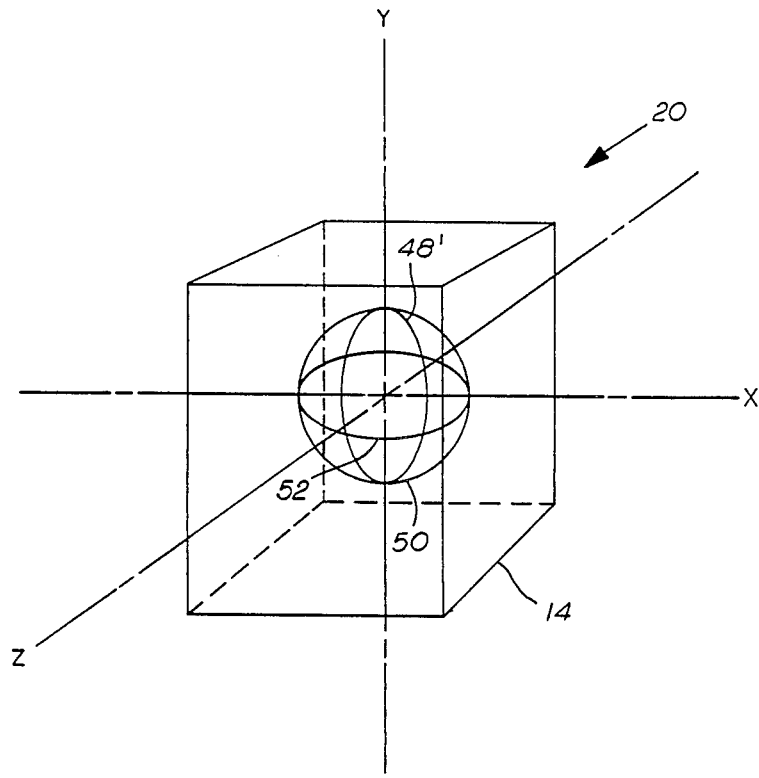
FIG. 2 is a diagram of the receiving coils.

As mentioned previously, the radiation source 20 is preferably located directly below a horizontal work surface 22. It is also preferred that the source 20 be centrally located with respect to the anticipated work area of surface 22. The work surface 22 is preferably made of a nonmetallic nonconducting material such as wood or plastic that does not distort or interfere with the propagation of electromagnetic radiation generated by the source 20. As schematically shown in FIG. 2(A) the source 20 preferably is comprised of three independent coiled antennas 48, 50 and 52, each of which induces a magnetic dipole field when energized. The three coils are oriented such that three orthogonal dipole magnetic fields are induced; each of the fields being identified with one of the X, Y, and Z axes defining a reference coordinate frame. The three coils 48-52 are sequentially energized by a transmitter located within the analyzing unit 18, through a cable 32. The transmitter applies an electrical signal across the cable 32 to generate the three dipole magnetic fields associated with the X, Y, and Z axes. As briefly mentioned above, the fields are sequentially generated because the electrical signals sent to the coils 48-52 are multiplexed so as to distinguish the dipole magnetic fields from each other.

Figure 2B:
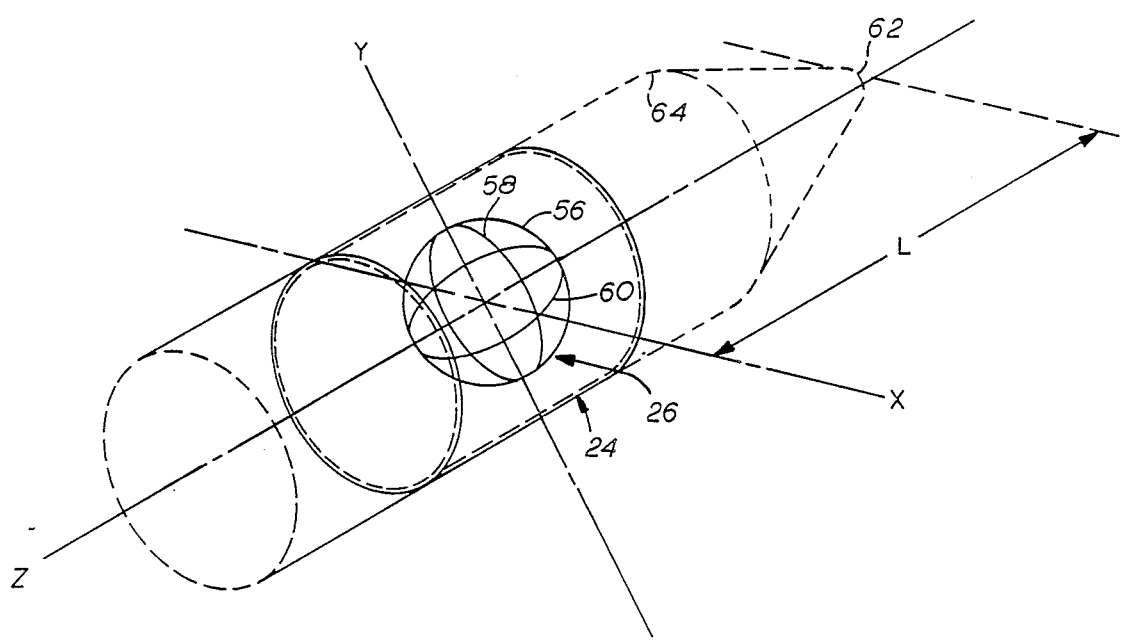

The antenna 26 located within the stylus 24 includes a plurality of receiving antenna 56, 58, 60 as generally shown in FIG. 2(B) for receiving components of the orthogonal electromagnetic fields induced by the source 20. Preferably, each of the receiving antenna is comprised of a coil of wire about an iron core. Just as in the source 20, each receiving coil 56-60 is oriented orthogonal to the others to define a sensor coordinate frame x, y and z. Each receiving coil 56-60 is operably coupled to the analyzing unit 18 by way of a cable 32. As seen in FIG. 2(B), the three receiving coils 56-60 are mounted in the stylus 24 where there is a known relationship L with respect to a tip 62 of a projection 64. The purpose of the projection 64 is to provide a point of contact which can be used to touch the surface of the core sample 40 and identify a point of contact between the core sample 40 and the stylus. Thus the stylus provides a means for identifying a plurality of points or coordinates within the reference coordinate frame generated by the source.

Figure 3:
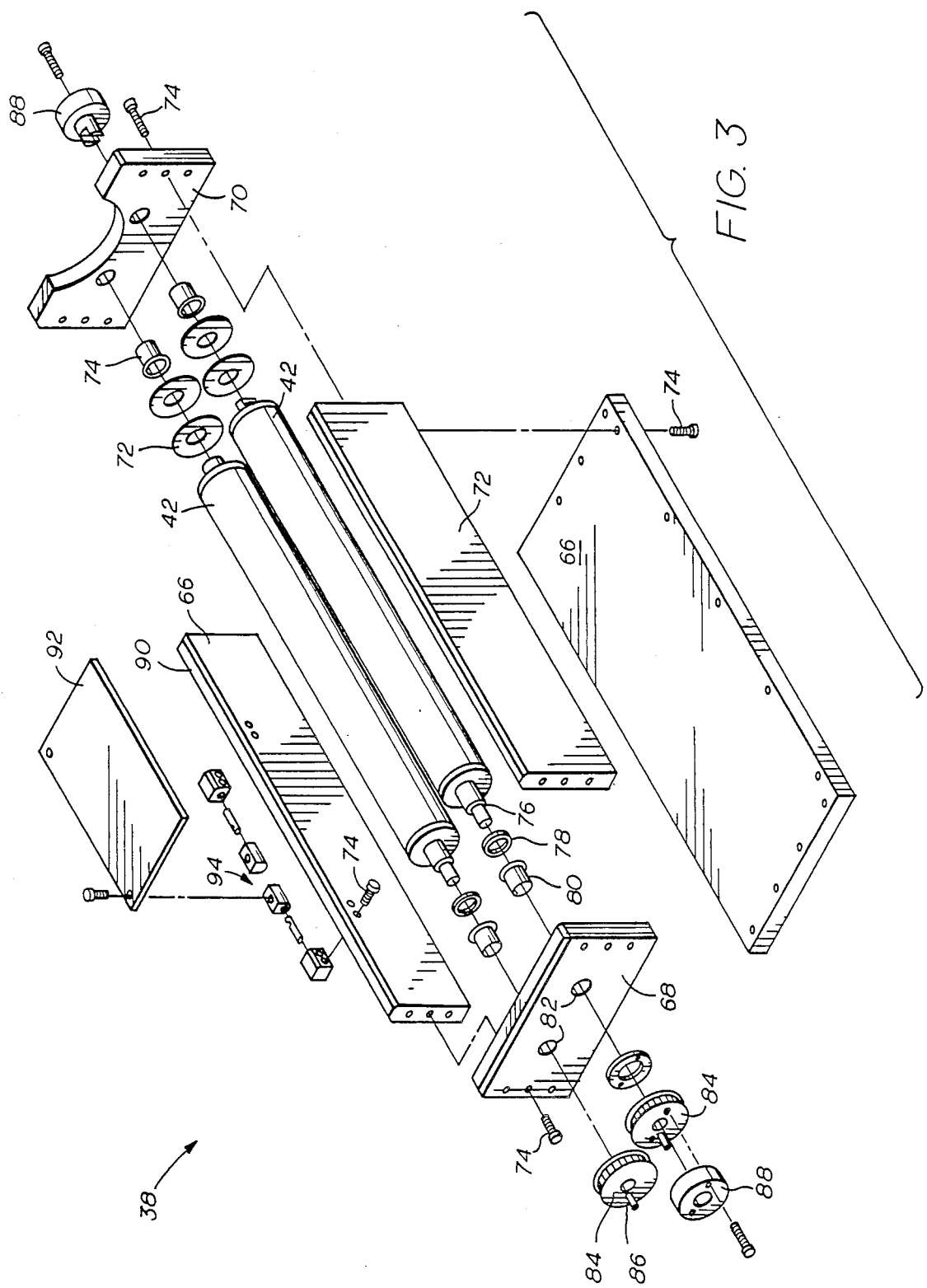
FIG. 3 is an exploded view of one embodiment of the core holder.

The core holder 38 is preferably located substantially symmetrical above the radiation source 20 and sitting on the working surface 22. The core holder, in one embodiment, is designed to horizontally receive a core sample up to a length of two feet. FIG. 3 is an exploded view of one embodiment of the core holder. As generally shown in the Figure, the core holder 38 may be comprised of two rollers 42 oriented horizontally and parallel to each other. Both rollers are supported above a base 66 by end walls 68 and 70, and side walls 72 held together in a box-like configuration by nylon screws 74. Each roller 42 has a shaft 76 which contains washers 78, and bearings 80 at each end and received by holes 82 in the end walls 68-70. The shafts of both rollers extend through end wall 68 and are received by gears 84 and held tight by keys such as 86. One of the rollers 42 may have knobs 88 anchored to each end of its shaft 76 for manual rotation. Symmetrically attached to the upper edge 90 of one of the sidewalls 72 may be a reference plate 92 which may be attached by a hinge such as indicated by 94. It is preferred that the reference plate be made of a transparent acrylic plastic so as not to obstruct the operator's view of the resting core sample in the core holder. It is also preferred that the rollers and all other components comprising the core holder be manufactured from nonconductive nonmetallic material such as polycarbonate plastics and or fiberglass. The rollers 42 are preferably covered with a high friction coefficient material such as 76-durometer moulded polyurethane to assure a non-slip rotation of a core sample under examination. The core holder as described above allows the operator to view both ends of the core sample as well as the external cylindrical surface without removing the core sample within the electromagnetic field. As mentioned previously, the core holder is mechanically coupled by belt 44 to a shaft encoder 46 located at a distance below the source 20. This is done because the encoder is metallic and may distort the induced electromagnetic fields, thus skew the coordinate frame.

Figure 4:
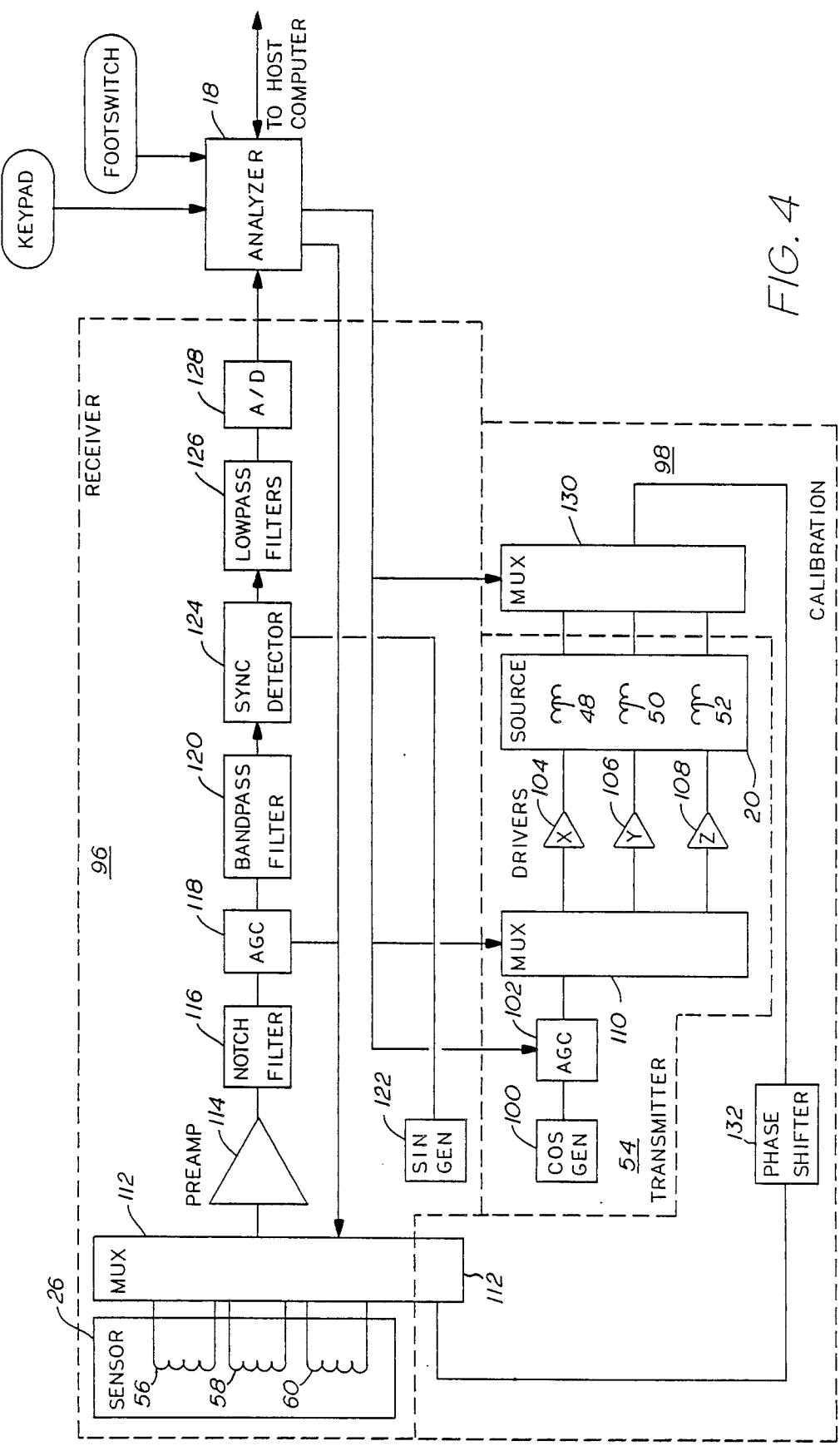
FIG. 4 is a schematic block diagram of the digitizer.
Figure 6A:
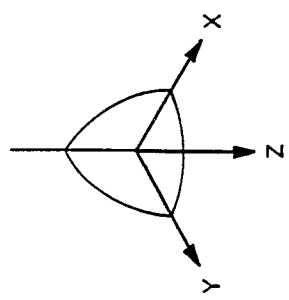
FIG. 6 illustrates a Euler angle sequence $\psi$, $\Theta$, $\phi$ which defines the orientation of the sensor.
Figure 6D:
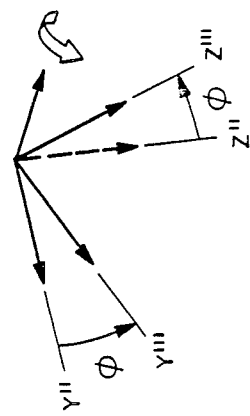

A schematic block diagram of the analyzing unit 18 of the present invention is illustrated in FIG. 4. The circuit is divided into three sections denoted by dashed lines, including the transmitter section 54, the receiver section 96 and calibration circuitry 98.

In the transmitter section 54, the signal transmitted by the source 20 is generated by a digitally synthesized cosine generator 100 at a frequency of 10285.71 Hz. A computer-controlled automatic gain control (AGC) circuit 102, working in conjunction with the receiver AGC circuitry, adjusts the output voltage of a set of drivers 104, 106, 108. This in turn varies the electromagnetic field generated by the source 20. A multiplexer 110 selects which of the three drivers is on. The three drivers 104–108, are identical and are functionally equivalent to high power op-amp current sources. The current source loads are the three coils 48, 50 and 52 of the source 20 and each one is capacitively tuned for 10285.71 Hz operation.

The receiver section 96 contains a differential input multiplexer 112 which selects one of the three coils of the sensor antenna 26 or a calibration signal for input to the rest of the receiver chain. This is followed by a low noise, high gain differential preamplifier 114. The signal is then passed through a notch filter 116, centered around the television horizontal synchronizer frequency (approximately 15.75 kHz) to enable the digitizer 16 to work in close proximity to cathode ray tube monitors. This is followed by another AGC stage 118 and a bandpass filter 120 centered around the system frequency of 10285.71 Hz. The output of the bandpass filter 120 is multiplied by a digitally-generated sine wave of 10285.71 Hz, generated at 22, in a synchronous demodulator 124. The sine wave is 90 degrees out of phase with the cosine generator 100 in the transmitter section 54. This is necessary because a complimentary 90 degree phase shift occurs between the transmission and reception of the digitizer carrier. The output of the synchronous demodulator 124 is a wave form whose DC component represents the desired system information. This is filtered by a seven pole, low pass filter 126 and digitized by a twelve bit analog-to-digital (A/D) converter 128. The A/D converter's digital output is then processed by the analyzing unit 18.

The calibration circuitry 98 removes most of the residual errors from the analog chain. A four input differential multiplexer 130 selects drive currents for measurement. The signal selected is divided down so as not to overload the preamplifier and is phase shifted at 132 by 90 degrees. It is selected for preamplifier input by the receiver differential input multiplexer 112. Measuring the three driver currents in the receiver section 96 allows gain variations to be measured and therefore normalized in software. Selecting the analog ground allows measurement of DC offset through the receiver section. This too is removed in software. It is important to understand that the analyzing unit is calibrated according to the configuration the source and stylus are to be deployed. For the purposes of this invention, once the source and stylus configuration was determined, the unit was returned to a division of the McDonnel Douglas Corporation where the device was specifically calibrated for the selected configuration.

The basic components of the system which determine the point and orientation of the stylus are the source of electromagnetic radiation 20, the antenna 26 in the stylus 24, which samples the electromagnetic fields, and the analyzing unit 18, which performs all required control calculation and interfacing tasks. The source 20 generates three orthogonal fields which are well defined in the area of interest. The fields are sampled by the antenna 26 and the resulting data are processed to determine the position and orientation of the antenna 26 relative to the three orthogonal fields. Source antennae, 48–52 creating dipole fields are preferred since they are symmetrical and relatively easy to describe analytically. Since the separation distance between the transmitter and receiver in the present application is relatively small, the near field component, or magnetic component, of electromagnetic radiation is used. Three loop antenna which each provide a singe magnetic dipole field are provided at the source 20. The three antenna at the source 20 are sequentially excited with an approximately 10 kHz carrier. This produces three orthogonal AC magnetic fields that induce signals in the three axes of the similarly constructed receiving antennas 56–60. The spacer outputs are filtered, synchronously detected and digitized to produce nine measurements. Each receiving antenna 56–60 produces three measurements, one from each of the transmitting coiled antennas 48–52 in the source 20. The analyzing unit 18 then processes these measurements to determine the six position and orientation unknowns of the stylus 2 relative to the source.

The design and operation of such remote object orientation and position determining systems is well defined in the prior art. Such systems have been used with either a far field or near field electromagnetic coupling as aircraft landing aids and as ordinance delivery systems for initially determining the line of sight of the pilot and directing computer guided ordinance to a desired target. Such systems are disclosed in prior U.S. Pat. Nos. 4,054,881 issued Oct. 18, 1977; 4,289,874 issued Nov. 3, 1981; 4,314,251 issued Feb. 2, 1982; 4,328,548 issued May 4, 1982; 4,346,384 issued Aug. 24, 1982; and 4,287,809 issued Sept. 8, 1981. The disclosures of these prior U.S. patents are hereby incorporated by reference. These prior patents teach how the components of the electromagnetic fields received by the receiving antenna 56–60 may be reduced to remote object orientation and position relative to the transmitting antenna in the source 20.

Figure 5:
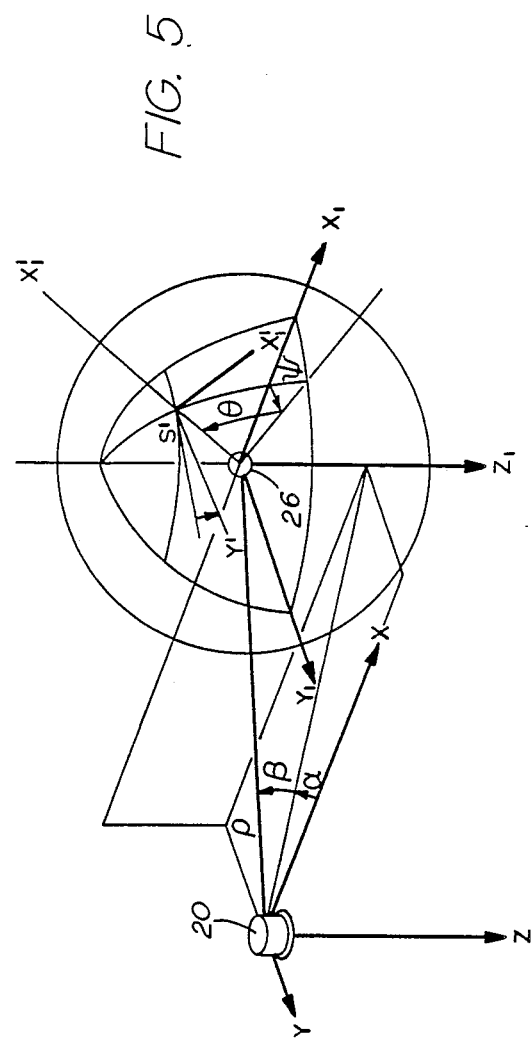
FIG. 5 illustrates the relationship between a three-axis source, and a three-axis sensor.

The goniometer of the present invention is a closed loop, all attitude six degree of freedom, position and orientation measurement system that tracks the position and orientation of the stylus 24. The goniometer of the present invention also tracks the longitudinal rotation angle of the core sample received by the core holder. The goniometer tracks the position and orientation of the stylus by determining small changes in the coordinates and then updating previous measurements. To accomplish this, the previous measurements are used to compute linear transformations that are approximately the inverse of those describing the true source-to-receiver coupling. With reference to FIG. 5, the position and orientation measurement system of the goniometer operates cooperatively between two independent coordinate frames, that of the source 20 (X, Y, Z) disposed in the work surface 22 and the receiving antenna 26 ($X_1$, $Y_1$, $Z_1$) disposed in the stylus 24. The system measures the two angles $\alpha$, $\beta$, that define the direction to the antenna 26 from the source and the three Euler angles ($\psi, \Theta, \phi$) that define the orientation of the antenna 26 relative to the source 20. As well as determining these five angular measurements, the system also provides range determining (ρ) determination, or the distance between the source 20 and the antenna 26. An inverted right-handed coordinate frame is used, the X axis is positive forward, the Y axis is positive to the right, and the Z axis is positive downward. The source coordinate frame X, Y, Z is defined by the central axes of the orthogonal loops comprising the source antenna triad. The source coordinate frame is defined during installation of the source 20 just below the work surface 22.

Figure 6C:
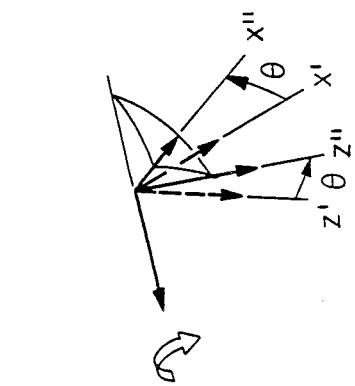
Figure 6B:
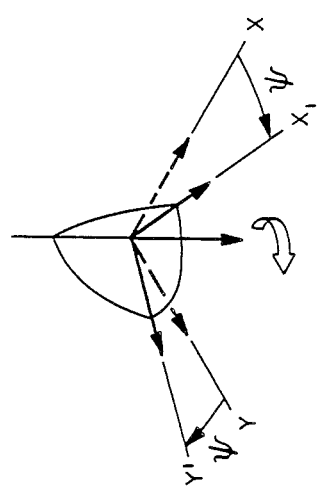

The antenna coordinate frame $X_1, Y_1, Z_1$ is defined by the central axes of the three orthogonal loops comprising the receiving antenna triad 56–60. The sensor position is specified in rectangular (x,y,z) or spherical $(\alpha,\beta,\rho)$ coordinates defined relative to the source coordinate frame. With reference to FIGS. 6A-6D it is illustrated that sensor orientation is specified by a sequence of three angular rotations. In FIG. 6B azimuthal rotation ($\psi$) first turns the sensor about, the Z' from X and Y to X' and Y'. The elevation rotation by $\Theta$ in FIG. 6C turns the sensor about the Y' axis from Z' and X' to Z'' and X''. The roll rotation ($\phi$) turns the sensor about the X'' axis from Y'' and Z'' to Y''' and Z''' in FIG. 6D. In the zero orientation condition, the three sensor axes are parallel to the corresponding source axes. The order or sequence of the rotations cannot be interchanged without changing the values of $\psi, \Theta$, and $\phi$.

Position and orientation are determined by solving for the six unknowns i.e. $\alpha,\beta,\rho,\psi,\Theta$, and $\phi$. This solution requires at least six independent measurements. The three axis transmitter and three axis receiver of the goniometer generates three vectors at the source which provide nine equations to solve for the six unknowns. In general, any six of the nine equations can be used to solve for the six unknowns.

With reference to FIG. 7, if $\overline{V}_1$ is the amplitude and direction of the magnetic field vector, and $\overline{V}_2$ is the amplitude and direction of the magnetic field vector at some position P in the field, then:

$$\overline{V}_2 = \overline{T} \, \overline{V}_1 \tag{1}$$

or $$\begin{bmatrix} x_2 \\ y_2 \\ z_2 \end{bmatrix} = T \begin{bmatrix} x_1 \\ y_1 \\ z_1 \end{bmatrix} \tag{2}$$

where $\overline{T}$ is the magnetic field transfer function which is a function of the coil geometry, the field shape and the position of $\overline{V}_2$:

$$\overline{T} = \frac{c}{\rho^3} \overline{T}_\rho^{-1} S \overline{T}_\rho \tag{3}$$

In Equation (3) C is a constant and represents the specific characteristics of the coil, that is coil diameter and the number of turns. ($\rho$) is the range or distance between the sensor antenna 26 and the source 20. $T_\rho$ and $T_\rho^{-1}$ are functions of the coil position and define the position of the coil in the field. If the coil is considered to be one of the sensor windings, $\overline{T}$ is a function of the two angles $\alpha$ and $\beta$ that define the position of the source 20 in relation to the sensor antenna 26.

If the sensor and source are perfectly aligned (the three axes are parallel to each other) S is defined as the field coupling between a sensor and a source in perfect alignment. When the source X axis is excited, the sensor picks up only along its $X_1$ axis. The sensor $Y_1$ and $Z_1$ axes are at right angles to the field and therefore do not pick up a signal. The same reasoning follows for the excitation of the source Y and Z axes. Therefore, $\overline{T}$ and $\overline{T}^{-1}$ relate to sensor rotations that deviate from the perfect sensor/source alignment situation.

With the aid of FIG. 8, the sensor transfer function can be developed. The heavy lines X and Z represent two axes of the sensor. For simplification, only the X and Z axes are illustrated. First consider the sensor at zero orientation, i.e., its azimuth elevation and roll angles are zero. The sensor is located at some position P in the magnetic field and the flux line 133 labelled "vector", includes the voltages in the coils. The voltage induced in the X axis is $X_1$ and the voltage induced in the Z axis is $Z_1$. Then, if the sensor is rotated through an elevation angle $\Theta$ to a new position, the new induced voltages are $X_2$ and $Z_2$ which are trigonometric functions of the elevation angle $\Theta$. An attitude transfer function $T_A$ can thus be defined for the new sensor position that is a function of the azimuth, elevation and roll. The transfer function $T_A$ relates a vector $V_2$ measured by a sensor at some attitude $(\psi,\Theta,\phi)$ to the vector $V_1$ measured by a sensor at zero attitude:

$$\overline{V}_2 = \overline{T}_A \overline{V}_1 \tag{4}$$

or $$\begin{bmatrix} x_2 \\ y_2 \\ z_2 \end{bmatrix} = T_A \begin{bmatrix} x_1 \\ y_1 \\ z_1 \end{bmatrix} \tag{5}$$

The transfer function $\overline{T}_A$ takes the form of a rotational sequence through the angles $\psi,\Theta,\phi$; or:

$$\overline{T}_A = \overline{T}_\phi \overline{T}_\Theta \overline{T}_\psi \tag{6}$$

If the sensor values at zero orientation are known, the sensor values can be computed at any sensor orientation by multiplying by $\overline{T}_A$.

FIG. 9 illustrates that the overall goniometer computational strategy is based on the fact that if the output is known, the input can be found by providing the inverse of the transformation, i.e., if $\overline{V}_2$ equals $\overline{T} \, \overline{V}_1$,; then $\overline{V}_1$ equals $\overline{T}^{-1} \, \overline{V}_2$. The transfer function T describes the length between the source and the sensor and is comprised of two parts;

$$T = T_{sensor} T_{field} \tag{7}$$

The sensor transfer function describes the sensor at zero orientation and provides the signals at any other orientation. The field transfer function describes the sensor at zero attitude and provides the sensor signals anywhere in the field. Therefore, the transfer function T describes what the sensor receives for a given transmitted vector.

If the transfer function is not known exactly (the position and orientation parameters $\alpha,\beta,\rho,\psi,\Theta,\phi$ are not exactly known) then the transmitted vectors do not match the recovered vectors exactly. If the position and orientation of the sensor is known exactly then inserting these angles in the transfer function equation makes it possible to recover the transmitted vectors. Using the information that the transmitted and received vectors are not the same, it is possible to generate new errors indicating that the position and orientation of the sensor has not been estimated correctly. These new errors are used to improve the estimation of the transfer function and continue in an iterative fashion.

In FIG. 9, the transmitted vectors are represented by $f_o$ and are the excitation of the three-axis source. The sensor picks up the magnetic signals. The gain control tries to boost the signal in order to maintain a constant signal at the sensor. This block removes the $C/p^3$ factor in Equation 3. After the signal has passed through electronic processing and been converted to a digital format, it reaches the analyzer 18 or central processing unit of the system.

The vectors sensed are the sensor transfer function $T_s$ and the field transfer function $T_f$. Mathematically, those inverse relationships are used to arrive at the value of S. If all of the transfer functions are estimated correctly, only S is left, which is the basic field coupling for the source and sensor when they are perfectly aligned. If the estimate is not correct, the value S is examined and error corrections are computed that are functions of the position and orientation errors. These errors are in the sensor frame. The errors measured in the sensor frame are then converted back to the source frame since this is where the position and orientation angles are defined. Once converted to the source frame, the errors are updated. The new estimates of the angles are equal to the old estimates plus the measured error. If the estimates of the position are not equal to the true position, a matrix develops terms which are functions of the position and orientation:

$$\bar{F} = \bar{T}_\rho \, \bar{T}_A^{-1} \, \bar{T}_A \, \bar{T}_\rho^{-1} \, S \, \bar{T}_\rho \, \bar{T}_\rho^{-1} \qquad (8)$$

or $$\bar{F} = \begin{bmatrix} 1 & \frac{3}{2}\Delta\alpha\phi & -\frac{1}{2}\Delta\alpha\phi - \frac{3}{2}\Delta\beta\phi + \frac{1}{2}\Delta\theta\phi \\ \frac{3}{2}\Delta\alpha\phi - \Delta\psi\phi & -\frac{1}{2} & -\frac{1}{2}\Delta\phi \\ -\frac{3}{2}\Delta\beta\phi + \Delta\theta\phi & \frac{1}{2\Delta\theta\phi} & -\frac{1}{2} \end{bmatrix} \qquad (9)$$

When all of the correct functions are arrived at, the restored tracking frame matrix with position and attitude errors, Equation 9, reduces down to the perfect field coupling matrix which describes the sensor in a pure dipole field.

$$S = \begin{bmatrix} 1 & 0 & 0 \\ 0 & -\frac{1}{2} & 0 \\ 0 & 0 & -\frac{1}{2} \end{bmatrix} \qquad (10)$$

The equations for the relationship between the stylus point 62 with respect to the source reference frame as follows. Discrepancies in the construction of the sensor stylus assembly are examined together with their effect on the basic coordinate equations.

Figure 10:
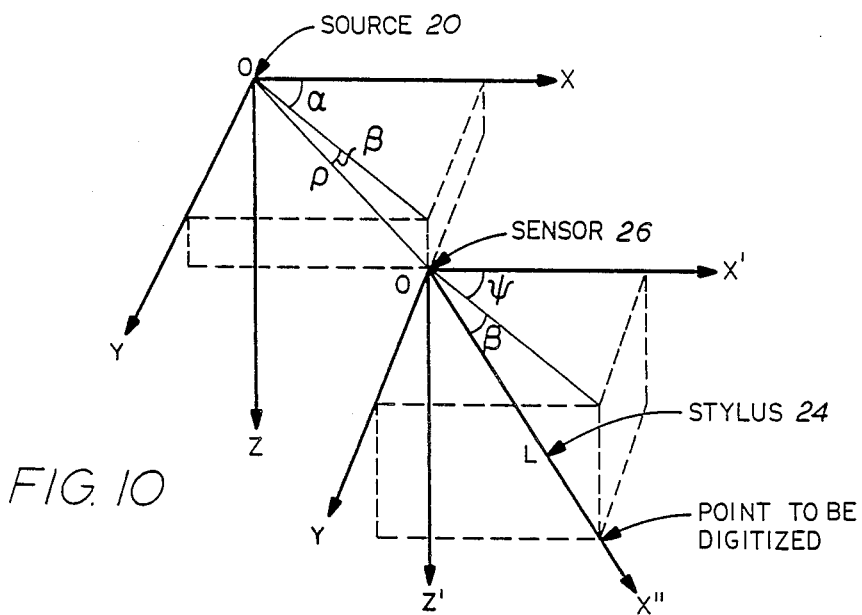
FIG. 10 represents the relationship between a three-axis source and a corresponding three-axis sensor.

FIG. 10 represents the relationship between a three-axis source and a corresponding three-axis sensor. The source 20 is located at the point 0 and defines the source reference frame X,Y,Z. The sensor 26 is located at the point O' with spherical coordinates $(\alpha,\beta,\rho)$ relative to the source coordinate frame. A sensor of zero orientation located at O' will have its axis parallel to the axis of the source reference frame and will define the translated X',Y',Z' reference frame. If the sensor is then rotated with respect to the X',Y',Z' reference frame, the orientation can be described by the Euler sequence $\psi,\Theta$ and $\phi$. The newly translated and rotated sensor axis can then be used to define the sensor reference frame X'',Y'',Z''.

Now consider a stylus of length L attached to the sensor and lying entirely along the "X" axis of the sensor reference frame. It is desired to represent the stylus point $(x''\rho, y''\rho, z''\rho)$ in terms of the source reference frame X,Y,Z.

Since the stylus lies along the "X" axis of the sensor reference frame, the point $(x''\ y''\ z'')$ may be represented by the vector.

$$\bar{T} = \begin{bmatrix} L \\ 0 \\ 0 \end{bmatrix}$$

in the sensor frame X'',Y'',Z''. A sequence of denotations through the Euler angles $\psi,\Theta,\phi$ applied to the vector V'' results in a new vector V' representing the coordinates of the tip of the stylus measured in the reference frame X',Y',Z' which is parallel to but translated from the radiator reference frame. In matrix notation:

$$\bar{V} = \bar{T}_{-\psi}\bar{T}_{-\Theta}\bar{T}_{-\phi}\bar{V}'' \qquad (11)$$

where each of the matrices $T_{-\psi}, T_{-\Theta}$ and $T_{-\phi}$ represent an inverse transformation through the respective Euler angle with:

$$\bar{T}_{-\phi} = \begin{bmatrix} 1 & 0 & 0 \\ 0 & \cos\phi & -\sin\phi \\ 0 & \sin\phi & \cos\phi \end{bmatrix} \qquad (12)$$

$$\bar{T}_{-\Theta} = \begin{bmatrix} \cos\theta & 0 & \sin\theta \\ 0 & 1 & 0 \\ -\sin\theta & 0 & \cos\theta \end{bmatrix} \qquad (13)$$

$$\bar{T}_{-\psi} = \begin{bmatrix} \cos & -\sin & 0 \\ \sin & \cos & 0 \\ 0 & 0 & 1 \end{bmatrix} \qquad (14)$$

A translation of the vector V', to the X,Y,Z radiator reference frame is then given by:

$$\bar{V} = \bar{T}_v + \bar{V} = \bar{T}_v + \bar{T}_{-\psi}\bar{T}_{-\theta}\bar{T}_{-\phi}\bar{V}' \quad (15)$$

$$\text{where } \bar{T}_v = \begin{bmatrix} \cos\alpha & \cos\beta \\ \sin\alpha & \cos\beta \\ & -\sin\beta \end{bmatrix}$$

represents the offset from the source to the sensor. Substituting Equations (11)–(14) into equation (15) and expanding yields:

$$x\rho = \cos\alpha \cos\beta + L \cos\cos\Theta \quad (16)$$

$$y\rho = \sin\alpha \cos\beta + L \sin\cos\Theta \quad (17)$$

$$z\rho = \sin\beta - L \sin\Theta \quad (18)$$

The point $(x\rho, y\rho, z\rho)$ represents the location of the tip of the stylus measured in the source reference frame.

Equations (16-18) assume that no errors in the calculation of the system variables $\alpha, \beta, \rho, \psi, \Theta,$ and $\phi$ or in the relationship of the stylus and sensor.

Errors in the construction of the sensor-stylus assembly may originated from either:

(a) A positional offset of the center of the sensor with respect to the long axis of the stylus, or;

(b) An error in the orientation of the sensor with respect to the stylus axis.

Figure 11:
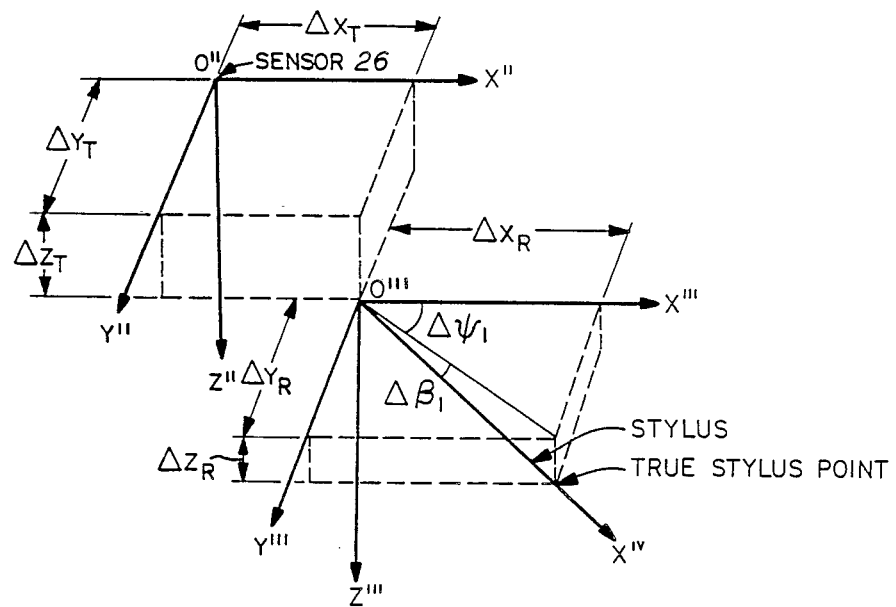
FIG. 11 is a geometrical representation of each source of error.

FIG. 11 is a geometrical representation of each source of error. The X",Y",Z" coordinate system is the same as the sensor reference frame represented in FIG. 10. In the case of an ideal sensor-stylus assembly, the long axis of the sensor would be entirely on the X" axis. The coordinates of the tip of the stylus would then be given by (L,O,O) measured in the sensor reference frame. In the case of a non-ideal sensor-stylus assembly, the coordinates of the stylus tip would be (L+$\Delta$x, $\Delta$y, $\Delta$z) where:

$$\Delta x = \Delta x, +\Delta x, \quad (19)$$

$$\Delta y = \Delta y, +\Delta y, \quad (20)$$

$$\Delta z = \Delta z, +\Delta z, \quad (21)$$

In these equations $\Delta$x, $\Delta$y, $\Delta$z, represent the contribution due to the offset error and $\Delta$x, $\Delta$y, $\Delta$z, represent the contribution from the orientation error in the sensor-stylus assembly.

In FIG. 11, the offset error is represented as a translation of the vector:

$$V = \begin{bmatrix} L \\ 0 \\ 0 \end{bmatrix}$$

to the point ($\Delta$x,$\Delta$y,$\Delta$z) measured in the sensor reference frame. This point defines the origin of a new coordinate system X",Y",Z". The axes of this system are parallel to the axis X",Y",Z" defining the sensor reference frame. Errors in the orientation of the sensor with respect to the long axis of the stylus can be represented as a rotation about the X",Y",Z" axis. The rotation may be represented by the Euler angle sequence $\Delta\psi_1$, $\Delta\Theta_1$, $\Delta\phi_1$ and defines a new coordinate system $X^{IV}, Y^{IV}$. The tip of the stylus is represented by the vector:

$$\begin{bmatrix} 1 \\ 0 \\ 0 \end{bmatrix}$$

in the translated and rotated coordinate system. If the vector:

$$\begin{bmatrix} 1 \\ 0 \\ 0 \end{bmatrix}$$

as measured in the $X^{IV}, Y^{IV}, Z^{IV}$ coordinate system is derotated through the Euler angle sequence $\Delta\psi, \Delta\Theta, \Delta\phi$, then a new vector defining the tip of the stylus in the X",Y",Z" reference frame results. The components of the new vector correspond to the rotational errors of Equations (19)–(21) and are given by:

$$\Delta x = 1 \cos\Delta\psi_1 \cos\Delta\Theta_1 \quad (22)$$

$$\Delta y = 1 \sin\psi_1 \cos\Delta\Theta_1 \quad (23)$$

$$\Delta z = 1 \sin\Delta\Theta_1 \quad (24)$$

Substituting Equations (22)–(24) into Equations (19)–(21) gives the errors of the sensor-stylus assembly measured in the sensor reference frame X",Y,"Z", i.e.:

$$\Delta x = \Delta x_1 - 1 \cos\Delta\psi_1 \cos\Delta\Theta_1 \quad (25)$$

$$\Delta y = \Delta y_1 - 1 \sin\Delta\psi_1 \cos\Delta\Theta_1 \quad (26)$$

$$\Delta z = -1 \sin\Delta\Theta_1 \quad (27)$$

Therefore, using Equation (15) the coordinates of the non-ideal sensor measured in the radiator reference frame is given by:

$$\bar{V} = \bar{T} + \bar{T}_{-\psi}\bar{T}_{-\theta}\bar{T}_{-\phi}\begin{bmatrix} L + \Delta x \\ \Delta y \\ \Delta z \end{bmatrix} \quad (28)$$

Equation 28 defines the coordinates of the stylus in the source reference frame under the assumption that no system errors exist in the calculation of the sensor position $(\alpha, \beta, \rho)$ and orientation $(\psi, \Theta, \phi)$. Existence of errors in these calculations would yield position and orientation values of the form $(\alpha+\Delta\alpha, \beta+\Delta\beta, \rho+\Delta\rho)$ and $(\psi+\Delta\psi, \Theta+\Delta\Theta, \phi+\Delta\phi)$, respectively. These errors are carried into the calculation of the stylus point coordinate yielding:

$$V = T_{v+\Delta v} + T_{-(\psi+\Delta\psi)}T_{-(\theta+\Delta\theta)}T_{-(\phi+\Delta\phi)}\begin{bmatrix} L - \Delta X \\ \Delta Y \\ \Delta Z \end{bmatrix} \quad (29)$$

in place of Equation 28 where each system variable $\alpha, \beta, \rho, \psi,$ is replaced by $\alpha+\Delta\alpha, \beta+\Delta\beta, \rho+\Delta\rho, \psi+\Delta\psi, \Theta+\Delta\Theta$ and $\phi+\Delta\phi$.

As briefly mentioned above, the analyzing unit 18, along with all the interconnecting source 20, antenna 26 and switching means 34 is interconnected to a processor unit or computer 28 such as an IBM-PC XT or similar type device. A software package developed by the assignee of this invention is used in the computer to control data acquisition. Through the use of menus, the software may direct the operator in the operation of the apparatus. That is to say, the software package may ask the operator to identify the particular points with the stylus 24 and activate the switch 34 to input those points into the computer memory. Based upon the data points received by the computer, a second software package performs subsequent data analysis, calculating the spatial orientation of the planar or linear structures and their depth along the core segment. This information may be displayed in many different ways. Rose diagrams, stereo plots, and tadpole or dip lots are just a few.

In a preferred mode of operation, the computer 28 and analyzing unit 18 are turned on. Before analyzing a core segment resting in the core holder 38, reference points must be identified within the electromagnetic field. The stylus is placed at each end of rollers 42 and these points input into the computer. These points at the ends of the rollers are used to initialize the system. The computer may next ask the operator to identify the top of the core segment using the stylus and ask for the depth the top of the core segment represents. The depth information may be input through the key pad 30 or with the aid of the mouse 36. After the top of the core has been identified, the bottom of the core is digitized with the stylus. The computer automatically calculates the length of the core segment as well as the representative depth.

The software may next ask the operator for data points used to calculate the core diameter, as well as to determine a reference line in calculating the amount of rotation and direction throughout the study. Many cores are oriented when taken from the hole. Vertical lines may be scratched along the length of the core, each separated from another by a known angle with respect to the axis of the core. To provide the computer with an azimuth oriented core, the operator need only identify several points along the azimuth marker scratched along the core. The azimuth is then entered into the computer which is stored. It is preferred that the azimuth marker along the length of the core be aligned directly under the edge defined by the acrylic reference plate 92 prior to identifying the azimuth. This serves two functions. First, it provides a reference line along the length of the core, used to calculate the core diameter. Second, it provides an azimuth or directional orientation to the core.

Once the reference is identified and input into the computer, the operator rotates the core by the handle on one of the rollers, one complete rotation so as to align the azimuth marker or initial reference line with the acrylic edge. The operator again identifies several points on the core sample along the azimuth marker at the edge of the acrylic reference plate 92. The amount of rotation of the core is detected by the shaft encoder 46 mechanically coupled to the rollers 42 by the belt 44. The shaft encoder output is passed to the computer 28 to determine the core diameter. Up to this point in the method, the goniometer 16 has determined the core length, the orientation of a line on the core with respect to a known reference point, and its diameter. The goniometer now monitors the rotation of the core about its longitudinal axis through the shaft encoder coupled to the rollers.

Once these parameters have been determined and stored in the computer, the operator may select by way of the computer menu the particular features to be identified. For example, the operator may wish to identify the fracture planes exhibited in the exterior surface of the core. Alternatively, the operator may elect to identify and determine the strike and dip of bedding planes. The operator may make his selection by using the key board or the mouse as mentioned earlier.

To identify a particular feature displayed along the core exterior, the operator simply places the tip of the stylus at preferably no less than five points along the feature; at each point activating the foot switch to input the data point on the computer. It is also preferred that the points be spaced from each other along the feature. The core may be rotated using the rollers if necessary to follow the identified feature. Up to as many as 20 points may be used to identify a single linear feature. Once a feature has been fully identified by the preferred number of points the operator indicates this by way of the key board or mouse. The software in the computer automatically calculates the respective characteristic of the feature and catalogs it in its memory. The process is repeated for each feature to be identified. Once all the desired features have been identified, the operator may elect to display the data in one of several output formats. The software package preferably allows this to be viewed on a computer screen periodically throughout the examination process. In addition, peripheral devices such as printers and plotters may be used to produce hard copies of the output.

It should be understood that the above method will work on slabbed core samples as well as full cylindrical cores. For slab cores, the samples are supported above the rollers by rings. The rings provide support to the slabbed core as it is rotated as well as allowing the operators full acess to the exterior surface of the core. The slabbed core adaptor rings are described below.

Figure 12:
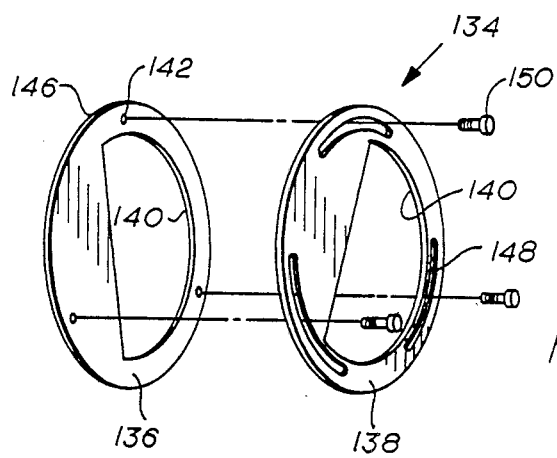
FIG. 12 is an exploded view of an adaptor ring for this invention.

FIG. 12 is an exploded view of one embodiment of the slab adaptor rings 134. Each ring 136 may be comprised of two members 138 and 138, each having a semicircular cutout portion 140. Member 136 may have a plurality of holes 142 located radially near its perimeter 146. Member 138 may have a plurality of slots 148 similarly located. Member 138 may be coupled adjacent to member 136 by fasteners 150 having threads extending through slots 148 and are screwed into holes 142. The fasteners may be loosened to allow partial rotation of one member with respect to the other; the amount of rotation limited only by the length of the slots 148.

Figure 13:
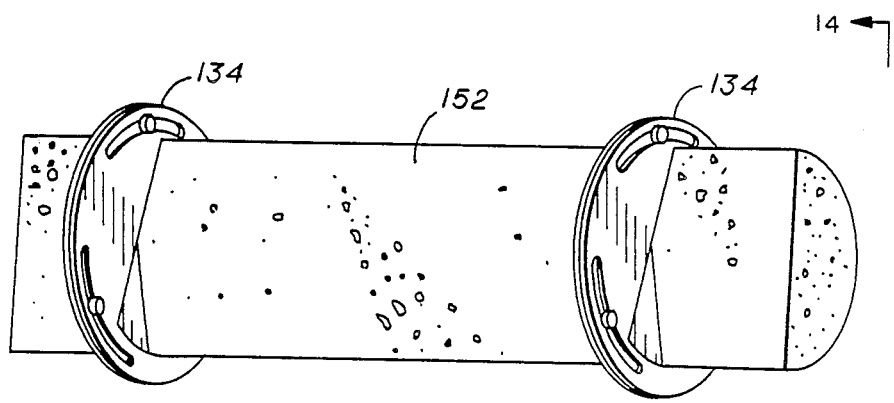
FIG. 13 is a perspective view of the adaptor ring holding a slabbed core.
Figure 14:
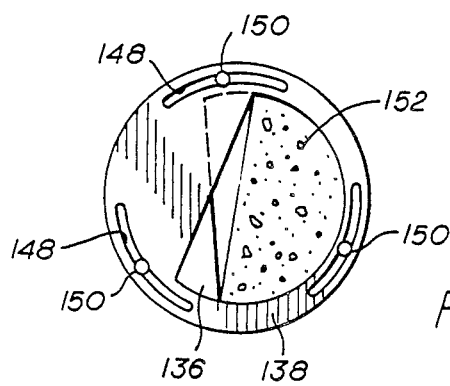
FIG. 14 is an end view of FIG. 13.

FIG. 13 is a perspective view of the adaptor rings supporting a slabbed core 152. FIG. 14 is an elevational view of FIG. 13 looking down the longitudinal axis of the core. As can be seen from the figures, the slabbed core sample 152 is fully supported by the adaptor rings 134. The two members 136 and 138 are partially rotated with respect to each other until the flat surface of the semi circular cutout 140 of each member contacts the core. This in effect clamps the core within the ring. The fasteners are tightened, locking member 136 against member 138. The slabbed core sample may be examined on the goniometer just as a cylindrical core sample: the rings providing complete rotation of the core 152.

It is preferred that the components of the adaptor ring be constructed of non-conductive materials similar to those comprising the core holder assembly described previously.

For illustrative purposes, our invention has been described with a certain degree of specificity. Variations will occur to those skilled in the art but which may be included within the scope and spirit of this invention which is limited only by the appended claims.

We claim as our invention:

1. An apparatus for digitally determining the spatial orientation of planar and linear structures exhibited in a three-dimensional body, comprising:
   (a) means for rotating said body about a longitudinal axis;
   (b) means coupled to said means for rotating, for measuring a rotation angle and rotation direction of said body about the axis;
   (c) means for generating orthogonal electromagnetic fields encompassing said body to define a spatial coordinate frame;
   (d) means for tracing said structures on said body to be digitally determined within the spatial coordinate frame;
   (e) means for detecting each of said orthogonal electromagnetic fields at a plurality of point along a trace, said detecting means mounted on said tracing means; and
   (f) analyzing means for energizing said means for sequentially generating the orthogonal electromagnetic fields, and for receiving an output from said detecting means and converting the output into a spatial coordinate.

2. An apparatus for digitizing and displaying the orientation of planar and linear structures in a core sample of the earth in three-dimensional space, comprising;
   (a) means for supporting the core sample above a work surface and rotating said core sample about a longitudinal axis defined by said core sample;
   (b) means, operably coupled to said means for rotating, for measuring a rotation angle and a rotation direction of said means for rotating;
   (c) means, symmetrically disposed and proximate to said means for rotating, for inducing orthogonal electromagnetic fields delineating a three-dimensional coordinate system encompassing said core sample;
   (d) stylus means for tracing a plurality of coordinates on said core sample located within said coordinate system, each of said coordinates represented by a point along a feature expressed along the external surface of said core sample;
   (e) means within said stylus means, for detecting each of said electromagnetic fields at each of said plurality of coordinates identified by said stylus means, each of said electromagnetic fields detected providing an output to define said plurality of coordinates in three dimensional space; and
   (f) processor means, interfaced with said means for measuring a rotation angle, means for inducing orthogonal electromagnetic fields, and said means for detecting, for calculating and displaying the three-dimensional coordinates defined by said means for detecting.

3. An apparatus as defined in claim 2, wherein the means for rotating said core sample comprises:
   (a) a support means;
   (b) roller means disposed within the supporting means for retaining the core sample thereon;
   (c) means for moving said roller means in unison and in the same rotational direction; and
   (d) reference means attached to the support means for measuring a beginning point and an ending point on the core sample.

4. An apparatus as defined in claim 2, wherein the means for measuring a rotation angle and rotation direction of the rotating means, comprises:
   (a) a shaft encoder spaced apart for the rotating means; and
   (b) a belt coupling the shaft encoder to the rotating means.

5. A method for electromagnetically digitizing surficial manifestations of planar and linear structures within a three-dimensional body, comprising the steps of:
   (a) orienting said body in a sequentially-generated orthogonal electromagnetic field, said electromagnetic field defining a three-dimensional coordinate framework about the body;
   (b) tracing the surficial manifestations along the exterior of said body with a stylus and identifying a plurality of coordinate points along each trace to locate the surficial manifestation within the three-dimensional framework;
   (c) rotating said three-dimensional body by a predetermined amount about its longitudinal axis, the angle and direction of rotation output to a processor for rotating the three-dimensional coordinate framework with respect to the body; and
   (d) processing and displaying the plurality of coordinate points identified by said stylus, indicating the orientation of the planar and linear structure within the three-dimensional body.

6. A method for obtaining the orientation of planar and linear features expressed along the external surface of a geologic material taken from the subsurface of the earth, comprising the steps of:
   (a) sequentially generating orthogonal electromagnetic fields about the geologic material, said fields defining a three-dimensional coordinate system enveloping the geologic material;
   (b) tracing the features expressed along the surface of the geologic material with a stylus and at a plurality of points along each feature identifying components of said fields defining the coordinate system, the components of said fields identified at each of said points output to a processor operably coupled to the stylus;
   (c) rotating the geologic material about an axis within said fields, the direction and amount of rotation detected by an encoder and output to said processor for use in rotating the three-dimensional coordinate system in correspondence with the direction and amount of rotation of the geologic material;
   (d) processing the components of the electromagnetic fields identified at the plurality of points along each feature traced on the geologic material to determine the orientation of each feature with respect to the geologic material and displaying the coordinates of said plurality of points, corrected for rotation, for each identified feature expressed along the surface of the geologic material.

7. A method for delineating the orientation of planar and linear structures expressed along an external surface of a core sample taken from the subsurface of the earth, comprising the steps of:
   (a) placing said core sample in sequentially-generated orthogonal electromagnetic fields, said fields defining a three-dimensional coordinate framework about said core sample;

(b) tracing surficial expressions of the planar and linear structures along the external surface of said core with a digitizing stylus and identifying a plurality of points along each surficial expression to establish the spatial orientation of said planar and linear structures;

(c) rotating said core sample about an axis, the direction and amount of rotation output to a processor for rotating the three-dimensional coordinate framework in correspondence with the rotation of the core sample; and (d) displaying the spatial orientation of said planar and linear structures.

8. An apparatus as defined in claim 1, further comprising:

(a) processing means operably coupled to said energizing and output receiving means, and to said measuring means, for storing each spatial coordinate; and (b) means operably coupled to said processing means, for displaying an output of the stored spatial coordinates.

9. An apparatus as defined by claim 8 further comprising:

(a) a nonconductive work surface upon which said means for rotating is resting;

(b) said means for generating disposed substantially symmetrically beneath said means for rotating and fixed beneath said work surface.

10. An apparatus as defined by claim 9, further comprising switching means distant from said work surface and operably coupled to enable said means for energizing the generating means and the detecting means.

11. An apparatus as defined in claim 9, wherein said means for rotating, comprises:

(a) means for supporting said body above the work surface;

(b) roller means disposed within said supporting means for retaining said body thereon;

(c) means for adapting said body to rotate around a preferred axis parallel to said roller means; and (d) means for moving said roller means in unison and in the same rotational direction.

12. An apparatus as defined in claim 11, further comprising (a) shaft encoder means for measuring a direction and rotation angle of the roller means; and (b) belt means coupling the encoder means to the roller means.

13. An apparatus as defined in claim 9 wherein said means for generating orthogonal electromagnetic fields, comprises:

(a) a plurality of antenna, each oriented orthogonal to one another so that orthogonal dipole magnetic fields are induced when energized.

14. An apparatus as defined in claim 1, wherein said stylus means for tracing comprises a housing having a projection defined for selecting a point of contact between said housing and the surface of said body, said housing also having a known relationship between said point of contact on said projection and said detecting means.

15. An apparatus as defined in claim 13, wherein said analyzer means for energizing the generating means and for receiving the output from said detecting means, comprises:

(a) a transmitter means for applying to said generating means electrical signals which generate the dipole magnetic fields, said electrical signals being multiplexed so as to distinguish the dipole magnetic fields from each other; and (b) a receiver means for receiving a multiplexed output from said detecting means, massaging said output and passing the output to said processing means.

16. An apparatus as defined in claim 8, wherein said processing means comprises a computer.

17. An apparatus as defined in claim 10, wherein said means for displaying comprises a cathode ray tube.

18. An apparatus as defined in claim 10, wherein said switching means comprises:

(a) a foot switch operably coupled to said analyzing means; and (b) a keypad operably coupled through said processing means to said analyzing means.

19. An apparatus as defined in claim 9, further comprising: means mounted on said supporting means, for providing a reference line so that a complete rotation of said body.

* * * * *

UNITED STATES PATENT AND TRADEMARK OFFICE
CERTIFICATE OF CORRECTION

PATENT NO. : 4845503
DATED : July 4, 1989
INVENTOR(S) : Hamish G. Adam, Peter J. Sharer and P. Eric Peterson It is certified that error appears in the above—identified patent and that said Letters Patent is hereby corrected as shown below:

In column 1, line 16, insert --a-- between "at" and "point"; on line 57, insert --a-- between "of" and "core".

In column 2, line 17, change "plane" to --planes--; on line 18, insert a hyphen between "cable" and "connected"; on line 41, insert a hyphen between "core" and "depth"; on line 52, change "features" to --feature's--.

In column 3, line 26, insert --a-- between "as" and "foot"; on line 28, insert a comma (,) after "28"; on line 39, change "1(b)" to --1(B)--.

In column 4, line 64, change "within" to --from--.
In column 5, line 35, change "22" to --122--.
In column 6, line 15, change "antenna" to --antennae--; delete "which"; on line 16, delete "three" and change "antenna" to --antennae--; on line 20, change "antennas" to --antennae--.
In column 6, line 27, change "2" to --24--.
In column 7, line 20, change "about, the Z'''" to -- about Z' --; on line 30, inset a comma (,) between "unknowns" and "i.e."; on line 60, insert --Rho-- between the period and ahead of the open parentheses.

In column 8, line 48, delete the semicolon (;), and on line 51, change the semicolon (;) to a colon (:).

UNITED STATES PATENT AND TRADEMARK OFFICE
CERTIFICATE OF CORRECTION

PATENT NO. : 4845503

DATED : July 4, 1989

INVENTOR(S) : Hamish G. Adam, Peter J. Sharer and P. Eric Peterson

It is certified that error appears in the above—identified patent and that said Letters Patent is hereby corrected as shown below:

In column 9, line 10, change "$C/p^3$" to --$C/^3$--; on lines 15-23, Equation (9) should read:

$$\bar{F} = \begin{bmatrix} 1 & \frac{3}{2}\Delta\alpha\phi - \frac{1}{2}\Delta\alpha\phi & -\frac{3}{2}\Delta B\phi + \frac{1}{2}\Delta\Theta\phi \\ \frac{3}{2}\Delta\alpha\phi - \Delta\psi\phi & -\frac{1}{2} & -\frac{1}{2}\Delta\phi \\ -\frac{3}{2}\Delta B\phi + \Delta\Theta\phi & \frac{1}{2}\Delta\Theta\phi & -\frac{1}{2} \end{bmatrix} \quad (9)$$

on line 46, change "...errors, Equation 9, reduces..." to read --...errors (Equation 9) reduces...--; on line 57, delete "as" on the end of that line; on line 58, change "follows." to --follow.--

In column 10, line 14, change the period to a colon;

UNITED STATES PATENT AND TRADEMARK OFFICE
CERTIFICATE OF CORRECTION

PATENT NO. : 4845503

DATED : July 4, 1989

INVENTOR(S) : Hamish G. Adam, Peter J. Sharer and P. Eric Peterson

It is certified that error appears in the above—identified patent and that said Letters Patent is hereby corrected as shown below:

In column 10, on lines 26 to just prior to Equation (12), should read:

— ... from the radiator reference frame. In matrix notation:

$$\bar{V} = \bar{T}_{-\psi} \bar{T}_{-\Theta} \bar{T}_{-\phi} \bar{V}'' \qquad (11)$$

where each of the matrices $\bar{T}_{-\psi}$, $\bar{T}_{-\Theta}$ and $\bar{T}_{-\phi}$ represent an inverse transformation through the respective Euler angle with: ... —.

In column 11, line 13, insert a comma between "expanding" and "yields"; in Equation (15), change "cosa" and "sina" to --cos $\alpha$ -- and -- sin $\alpha$ --, respectively; in Equation (15), change "-sin $\beta$" to -- $-\rho$ sin $\beta$ --; on line 11, insert a comma after "expanding" and "yields"; rewrite Equations (16)-(18) as follows:

UNITED STATES PATENT AND TRADEMARK OFFICE
CERTIFICATE OF CORRECTION

PATENT NO. : 4845503
DATED : July 4, 1989
INVENTOR(S) : Hamish G. Adam, Peter J. Sharer and P. Eric Peterson It is certified that error appears in the above—identified patent and that said Letters Patent is hereby corrected as shown below:

$$x_\rho = \rho \cos \alpha \cos \beta + L \cos \psi \cos \theta \qquad (16)$$

$$y_\rho = \rho \sin \alpha \cos \beta + L \sin \psi \cos \theta \qquad (17)$$

$$z_\rho = -\rho \sin \beta - L \sin \theta \qquad (18)$$

on line 27, change "originated" to --originate--; on line 29, change "stylus, or;" to --stylus; or--; Equations (19)-(21) should read as follows:

$$\Delta x = \Delta x_t + \Delta x_r \qquad (19)$$

$$\Delta y = \Delta y_t + \Delta y_r \qquad (20)$$

$$\Delta z = \Delta z_t + \Delta z_r \qquad (21)$$

on line 49, change " $\Delta x, \Delta y, \Delta z,$" to -- $\Delta x_t, \Delta y_t, \Delta z_t,$ --; on line 50, change " $\Delta x, \Delta y, \Delta z,$" to -- $\Delta x_r, \Delta y_r, \Delta z_r,$ --; on lines 64 and 67, change "axis" to --axes--.

In column 12, line 31, change "...X", Y,"Z", i.e.:" to --...X", Y", Z", i.e.:--.

In column 13, line 14, change "lots" to --plots--; on line 21, change "These points" to --The points--.

In column 14, line 41, change "136" to --134--; on line 42, change the first occurrence of "138" to --136--; on line 59, change "semi circular" to --semicircular--; on line 63, change the colon after "sample" to a comma.

UNITED STATES PATENT AND TRADEMARK OFFICE
CERTIFICATE OF CORRECTION

PATENT NO. : 4845503
DATED : July 4, 1989
INVENTOR(S) : Hamish G. Adam, Peter J. Sharer and P. Eric Peterson It is certified that error appears in the above—identified patent and that said Letters Patent is hereby corrected as shown below:

In the claims:

In claim 1, line 22, change "point" to --points--.

In claim 4, line 4, change "for" to --from--.

Signed and Sealed this

Twenty-eighth Day of May, 1991

*Attest:*

HARRY F. MANBECK, JR.

*Attesting Officer*  *Commissioner of Patents and Trademarks*